(12) United States Patent
Ogawa et al.

(10) Patent No.: US 8,900,626 B2
(45) Date of Patent: Dec. 2, 2014

(54) TRANSDERMAL DRUG DELIVERY SYSTEM AND METHOD OF USING THE SAME

(75) Inventors: Takahiro Ogawa, Woodland Hills, CA (US); Akiharu Isowaki, Woodland Hills, CA (US)

(73) Assignee: Senju USA, Inc., Woodland Hills, CA (US)

( * ) Notice: Subject to any disclaimer, the term of this patent is extended or adjusted under 35 U.S.C. 154(b) by 84 days.

(21) Appl. No.: 13/164,037

(22) Filed: Jun. 20, 2011

(65) Prior Publication Data
US 2012/0321673 A1  Dec. 20, 2012

(51) Int. Cl.
| | |
|---|---|
| A61F 13/02 | (2006.01) |
| A61K 31/56 | (2006.01) |
| A61K 9/70 | (2006.01) |
| A61K 9/00 | (2006.01) |
| A61K 31/58 | (2006.01) |
| A61K 31/573 | (2006.01) |

(52) U.S. Cl.
CPC .............. *A61K 9/0014* (2013.01); *A61K 31/56* (2013.01); *A61K 9/7053* (2013.01); *A61K 31/58* (2013.01); *A61K 9/0048* (2013.01); *A61K 31/573* (2013.01)
USPC .......................................... 424/448; 424/449

(58) Field of Classification Search
USPC ................................. 424/448, 449
See application file for complete search history.

(56) References Cited

U.S. PATENT DOCUMENTS

| | | | |
|---|---|---|---|
| 3,721,687 A | 3/1973 | Elks | |
| 4,158,055 A | 6/1979 | Shultz et al. | |
| 4,666,441 A | 5/1987 | Andriola et al. | |
| 4,954,343 A * | 9/1990 | Hosaka et al. | 424/448 |
| 6,132,751 A * | 10/2000 | Suzuki et al. | 424/422 |
| 6,991,095 B1 * | 1/2006 | Yamasoto et al. | 206/204 |
| 7,052,714 B1 | 5/2006 | Tojo et al. | |
| 2005/0245497 A1 * | 11/2005 | Penfold et al. | 514/179 |
| 2006/0036220 A1 | 2/2006 | Kawahara et al. | |
| 2007/0053964 A1 | 3/2007 | Isowaki et al. | |
| 2009/0082381 A1 | 3/2009 | Isowaki et al. | |
| 2009/0143359 A1 | 6/2009 | Isowaki et al. | |
| 2009/0209632 A1 | 8/2009 | Isowaki et al. | |
| 2009/0297590 A1 | 12/2009 | Yamaji et al. | |
| 2009/0318422 A1 | 12/2009 | Isowaki et al. | |
| 2010/0150992 A1 * | 6/2010 | Kawahara et al. | 424/448 |
| 2010/0160293 A1 | 6/2010 | Tojo et al. | |
| 2010/0227842 A1 | 9/2010 | Bowman et al. | |
| 2011/0028880 A1 | 2/2011 | Uchida et al. | |
| 2011/0104206 A1 | 5/2011 | Nanduri et al. | |

FOREIGN PATENT DOCUMENTS

| | | |
|---|---|---|
| GB | 1047519 | 11/1966 |
| WO | 89/03390 | 4/1989 |
| WO | WO-2005/060540 A2 * | 7/2005 |
| WO | 2008/026756 | 3/2008 |
| WO | 2009/145801 | 12/2009 |
| WO | 2010/102031 | 9/2010 |

OTHER PUBLICATIONS

Lee, Yoon Jung, et al., "Ocular Hypertensive Response to Topical Dexamethasone Ointment in Children", Korean Journal of Ophthalmology, vol. 20, No. 3, 2006, pp. 166-170.
Barlett, Jimmy D., et al., "Clinical Ocular Pharmacology", 5th Edition, 2008, pp. 229-233 and 390-391.
Druzgala, P., et al., "Soft Drugs—10. Blanching Activity and Receptor Binding Affinity of a New Type of Glucocorticoid: Loteprednol Etabonate", J. Steroid Biochem. Molec. Biol., vol. 38, No. 2, 1991, pp. 149-154.
International Search Report and Written Opinion issued Aug. 29, 2012 in corresponding International (PCT) Application No. PCT/US12/43126.
Package insert, Cordran® Tape, Flurandrenolide Tape, 4 μg/cm$^2$, Watson Pharma, Inc., FDA approval date Jul. 29, 1969.
Package insert, Drenison®, Fludroxycortide Tape, 4 μg/cm$^2$, Manufactured and Marketed by Dainippon Sumitomo Pharma Co., Ltd, marketed in Japan Apr. 1973, with partial English translation.
Package insert, Tokuderm® tape, Betamethasone valerate, 6 μg/cm$^2$, Marketed by Taiho Pharmaceutical Co., Ltd., Manufactured and Marketed by Nichiban Co., Ltd., marketed in Japan Jun. 1992, with partial English translation.
Package insert, Eclar® Plaster 20 μg/cm$^2$, Deprodone Propionate Plaster, Manufactured and Marketed by Hisamitsu Pharmaceutical Co., Inc., marketed in Japan Jul. 2001, with partial English translation.

* cited by examiner

*Primary Examiner* — Ali Soroush
(74) *Attorney, Agent, or Firm* — Wenderoth, Lind & Ponack, L.L.P.

(57) ABSTRACT

A transdermal drug delivery system comprising a steroid as an active agent, wherein the steroid may be clobetasol propionate, betamethasone dipropionate, amcinonide, or loteprednol etabonate. The transdermal drug delivery system also comprises a pressure-sensitive adhesive layer and a support, wherein the steroid is present in the pressure-sensitive adhesive layer, and wherein the pressure-sensitive adhesive layer is provided on a support. The transdermal drug delivery system may be applied onto the eyelid of a patient in need thereof, in order to treat a disease of the eyelid, such as chalazion, blepharitis or meibomian gland dysfunction.

14 Claims, 1 Drawing Sheet

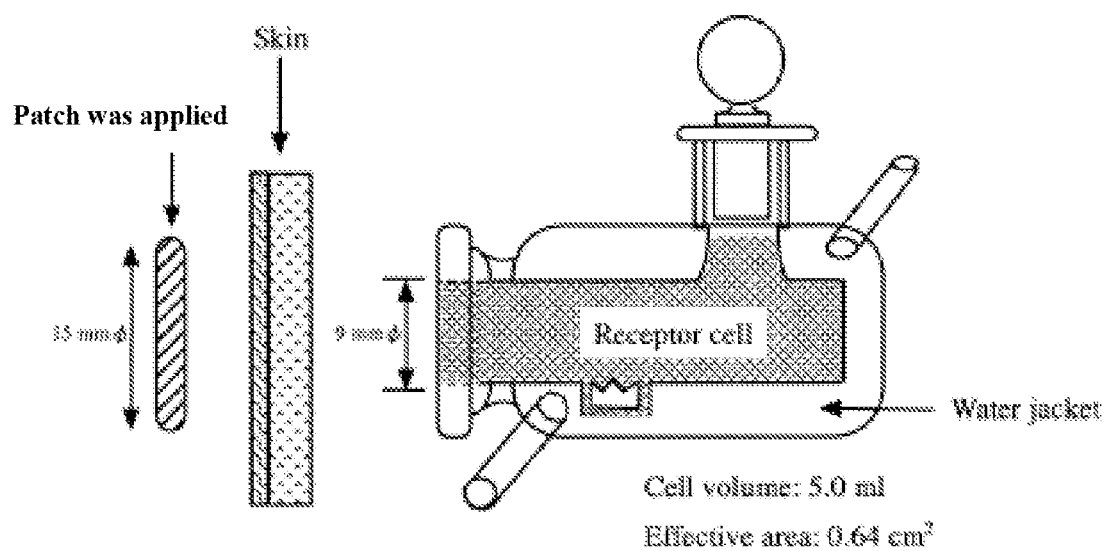
**Experimental Apparatus for *In Vitro* Permeation Experiment**

TRANSDERMAL DRUG DELIVERY SYSTEM AND METHOD OF USING THE SAME

FIELD OF THE INVENTION

The present invention relates to a transdermal drug delivery system, and a method for treating diseases of the eyelid by applying the transdermal drug delivery system to the eyelid of a patient in need thereof.

BACKGROUND OF THE INVENTION

Transdermal drug delivery systems, also known as transdermal or skin patches, are medicated adhesive patches that are placed on the skin to deliver medication through the skin by percutaneous absorption, which is the process of absorption through the skin from topical application. The transdermal drug delivery system may deliver the medication systemically, i.e., through the bloodstream, or may deliver the medication topically by placement on the desired treatment site.

Diseases of the eyelid, such as chalazion, blepharitis, meibomian gland dysfunction, allergic conjunctivitis, vernal keratoconjunctivitis and atopic keratoconjunctivitis are generally recognized as a result of inflammation. There are no FDA approved medications for treatment of chalazion, blepharitis, and meibomian gland dysfunction, although steroid treatment may be used for treatment. Steroid treatment is provided in the form of an ophthalmic steroid ointment as an anti-inflammatory drug.

A chalazion is a chronic, sterile, lipogranulomatous inflammation due to retention of meibomian gland secretion. The lesion usually develops over several weeks, and is more common in the upper eyelid, appearing as a hard, painless immobile mass. Chalazia that fail to respond to conservative management, i.e., topical installation of antibiotic and steroid eye drops, may be treated with an intralesional injection of steroids, where 0.1 to 0.2 ml of triamcinolone acetonide is injected into the center of the lesion. Chalazia typically resolve within two weeks after a single injection of steroid, but larger lesions (>6 mm in diameter) require a second injection. The overall success rate is 77% to 93% after one or two injections. If the chalazion persists after the second injection, surgical excision and curettage are required.

However, there are complications after steroid injection, such as discomfort at the injection site, formation of subcutaneous white (steroid) deposits in the treated area, depigmentation of the eyelid at the injection site, and skin atrophy. Very rarely, retinal and choroidal vascular occlusion after the steroid injection may occur. If, after one or two months of conservative therapy, or two to four weeks of intralesional steroid injection, the chalazion has not resolved, surgical resection may be recommended.

Blepharitis is a common and persistent inflammation of the eyelids. Symptoms include irritation, itching and occasionally red eye. Blepharitis frequently occurs in people who have oily skin, dandruff or dry eyes. Bacteria are on the surface of everyone's skin, but thrive in the skin at the base of the eyelashes in certain individuals. The resulting irritation, which is sometimes associated with over activity of the nearby oil glands, causes dandruff-like scales and particles to form along the lashes and eyelid margins. For some people, the scales or bacteria associated with blepharitis produce only minor irritation and itching, but in others it may cause redness, stinging or burning. Some people may develop an allergy to the scales or to the bacteria which surround them. This can lead to a more serious complication with inflammation of other eye tissues, particularly the cornea.

There are many medications and treatments available for blepharitis, including antibiotic and steroid preparations in the form of drops or ointments. While steroid medications often hasten relief of symptoms, long-term use can cause some harmful side effects. Once the acute phase of blepharitis is overcome (after several weeks), milder medications may be helpful, or no medications may be necessary to control the eyelid inflammation.

Meibomian gland dysfunction (MGD), also known as posterior blepharitis, is one of the most common physical findings in primary eyecare patients. It is important to treat MGD for several reasons. First, while MGD may not threaten sight, it undermines the patient's quality of life. Second, the abnormal lipids produced by MGD patients have a negative effect on the quality of the tear film, which produces both discomfort and visual acuity problems. Third, MGD can lead to chalazia, which can be painful and unsightly for the patient. MGD is also very highly associated with infections of the lid margins, so it may contribute to bacterial growth in the lids, which can increase the risk of infection following any kind of ocular surgery. Lastly, for many patients, MGD makes wearing contact lenses very difficult.

Topical lid hygiene comprises a first-line therapy. If additional therapy is needed, an oral tetracycline (minocycline or doxycycline) may be added. If additional anti-inflammatory effect is needed, topical cyclosporine (Restasis®; Allergan) and/or a topical corticosteroid may be added.

However, it is reported that ophthalmic steroid ointments can be associated with serious side effects. Steroid ointments are prescribed for long term to chronic diseases, because the penetration (permeation) is poor. Accordingly, the long-term use of an ophthalmic steroid ointment is likely to induce serious adverse events, such as an increase in intraocular pressure (IOP), which may result in ocular hypertension or glaucoma, or induce loss of sight; posterior subcapsular cataracts; retardation of corneal epithelial healing; corticosteroid uveitis; mydriasis and ptosis; infection; and other side effects such as transient ocular discomfort and steroid-induced calcium deposits. Please see Bartlett, Jimmy, et al., Clinical Ocular Pharmacology, Fifth Edition, 2008, pages 229-233, the contents of which are incorporated herein by reference.

Some patients are "steroid responders," so they experience increased postoperative IOP as a result of their medications. Withdrawal of the steroid usually results in IOP returning to baseline within two to four weeks. In the case of an elevated IOP, conventional glaucoma medications may also be prescribed to manage this.

Topical steroid use may induce cataract formation, an inhibition of corneal epithelial or stromal healing, punctate staining and worsening of infection and herpes. Moreover, long-term use of topical steroids can lead to secondary infection with fungus or bacteria.

Allergic conjunctivitis is an inflammation of the tissue lining the eyelids, i.e., the conjunctiva, due to an allergy. When the eye is exposed to something to which a patient is allergic, histamine is released and the blood vessels in the conjunctiva become swollen, causing reddening of the eye (mainly due to vasodilation of the peripheral small blood vessels), oedema of the conjunctiva, itching and increased lacrimation (production of tears).

Generally, treatment of allergic conjunctivitis is to avoid the allergen. Additional treatments include administration of topical antihistamines (in the form of eye drops) or systemic antihistamines (in the form of a tablet), anti-inflammatory eye drops, mild steroid preparations applied directly onto the surface of the eye for severe reactions, or eye drops which stabilize mast cells (prevent the cells from releasing histamine). In serious cases of conjunctivitis, a strong steroid is necessary to treat the conjunctivitis as quickly as possible. However, as discussed previously, steroid ointments, as well as steroid eye drops, may result in serious side effects, such as an increase in IOP and cataracts, if employed for long term use.

Keratoconjunctivitis is an inflammation of the cornea and conjunctiva. Atopic keratoconjunctivitis is one manifestation of atopy, or a hypersensitive allergy. Vernal keratoconjunctivitis refers to keratoconjunctivitis occurring in the spring season, and is usually a result of allergens.

In view of the above, effective and safe treatments for eyelid diseases such as chalazion, blepharitis, meibomian gland dysfunction, allergic conjunctivitis, vernal keratoconjunctivitis and atopic keratoconjunctivitis are widely desirable.

U.S. Patent Publication No. 2010/150992 and U.S. Patent Publication No. 2006/036220 disclose a transdermal drug delivery system for treatment of ophthalmic diseases. However, these documents do not mention a method of treatment an eyelid disease, such as chalazion, blepharitis or meibomian gland dysfunction, by administering a steroid to a patient in need thereof.

U.S. Patent Publication No. 2009/209632 discloses a percutaneously absorptive preparation for preventing or treating allergic eye disease, which comprises olopatadine or a salt thereof as an active ingredient, and U.S Patent Publication No. 2009/143359 discloses a percutaneously absorptive preparation for preventing or treating allergic eye disease, which comprises epinastine or a salt thereof as an active ingredient. However, these documents particularly specify the use of olopatadine or epinastine as the active ingredient.

U.S. Patent Publication No. 2007/053964 discloses a percutaneous absorption type ophthalmic preparation comprising a muscarinic receptor agonist. However, this document specifies the use of a muscarinic receptor agonist as an active ingredient.

U.S. Patent Publication 2009/318422 discloses an ophthalmic percutaneous absorption type preparation comprising an ophthalmic drug and a vasoconstrictor in combination. However, this document specifies a combination of an ophthalmic drug and a vasoconstrictor.

U.S. Patent Publication No. 2009/082381 discloses a percutaneously absorbable ophthalmic preparation comprising a heterocyclic spiro compound or a salt thereof, to be administered to the eyelid skin surface to promote lacrimation. However, this document specifies a heterocyclic spiro compound or a salt as an active ingredient.

U.S. Pat. No. 7,052,714 discloses an ophthalmic adhesive preparation for percutaneous absorption to be used in treating diseases in the posterior parts of eye. However, this document specifies treatment for diseases in the posterior portion of the eye.

U.S. Patent Publication No. 2010/227842 discloses a method of treating blepharitis including administering a glucocorticoid in an ophthalmically acceptable vehicle. However, this document specifies an ophthalmic solution, rather than a patch.

The contents of U.S. Patent Publication No. 2010/227842, U.S Patent Publication No. 2009/143359, U.S. Patent Publication No. 2009/209632, U.S. Patent Publication No. 2007/053964, U.S. Patent Publication No. 2010/150992, U.S. Patent Publication No. 2006/036220, U.S. Pat. No. 7,052,714, U.S. Patent Publication 2009/318422 and U.S. Patent Publication No. 2009/082381 are incorporated herein by reference.

OBJECT OF THE INVENTION

An object of the invention is to provide a transdermal drug delivery system, and a method for topically treating diseases of the eyelid by applying the transdermal drug delivery system to the eyelid of a patient in need thereof. The method results in increased penetration of the active agent in the transdermal drug delivery system to the eyelid, thus providing a more effective and safer treatment than the prior art methods.

SUMMARY OF THE INVENTION

The present inventors have studied transdermal drug delivery systems in order to determine the efficacy and safety thereof. The present inventors have discovered that steroid patches comprising steroids such as amcinonide, loteprednol, betamethasone, and clobetasol demonstrated better efficacy and safety than ophthalmic ointments. This invention describes the formulation of such steroid patches and a method for treatment of ocular diseases.

Accordingly, the present invention provides:

(1) A transdermal drug delivery system for treatment of an eyelid disease comprising a pressure sensitive adhesive layer provided on a support, wherein the pressure sensitive adhesive layer comprises a steroid, and wherein the system is topically applied to a skin surface of an eyelid of a patient in need of the treatment.

(2) The transdermal drug delivery system according to the above (1), wherein the pressure-sensitive adhesive layer is selected from the group consisting of an acrylic pressure sensitive adhesive layer, a rubber-based pressure sensitive adhesive layer and a silicone-based pressure sensitive adhesive layer.

(3) The transdermal drug delivery system according to the above (2), wherein the pressure-sensitive adhesive layer is an acrylic pressure sensitive adhesive layer.

(4) The transdermal drug delivery system according to the above (1), wherein the steroid is selected from the group consisting of clobetasol propionate, clobetasol butyrate, betamethasone dipropionate, amcinonide, and loteprednol etabonate.

(5) The transdermal drug delivery system according to the above (4), wherein the steroid is selected from the group consisting of clobetasol propionate and clobetasol butyrate.

(6) The transdermal drug delivery system according to the above (4), wherein the concentration of the steroid is 0.005 to 5 w/w % of the total weight of the transdermal drug delivery system.

(7) The transdermal drug delivery system according to the above (1), wherein the eyelid disease is at least one selected from the group consisting of chalazion, blepharitis and meibomian gland dysfunction.

(8) A transdermal drug delivery system for treatment of at least one eyelid disease selected from the group consisting of chalazion, blepharitis and meibomian gland dysfunction comprising an acrylic pressure sensitive adhesive provided on a support, wherein the acrylic pressure sensitive adhesive comprises clobetasol propionate, and wherein the system is topically applied to a skin surface of an eyelid of a patient in need of the treatment.

(9) A method for treatment of an eyelid disease, comprising topically administering a transdermal drug delivery system to a skin surface of an eyelid of a patient in need thereof, wherein the transdermal drug delivery system comprises a pressure sensitive adhesive layer provided on a support, and wherein the pressure sensitive adhesive layer comprises a steroid.

(10) The method for treatment of an eyelid disease according to the above (9), wherein the pressure-sensitive adhesive layer is selected from the group consisting of an acrylic pressure sensitive adhesive layer, a rubber-based pressure sensitive adhesive layer and a silicone-based pressure sensitive adhesive layer.

(11) The method for treatment of eyelid disease according to the above (10), wherein the pressure-sensitive adhesive layer is an acrylic pressure sensitive adhesive layer.

(12) The method for treatment of an eyelid disease according to the above (9), wherein the steroid is selected from the group consisting of clobetasol propionate, clobetasol butyrate, betamethasone dipropionate, amcinonide, and loteprednol etabonate.

(13) The method for treatment of an eyelid disease according to the above (12), wherein the steroid is selected from the group consisting of clobetasol propionate and clobetasol butyrate.

(14) The method for treatment of an eyelid disease according to the above (12), wherein the concentration of the steroid is 0.005 to 5 w/w % of the total weight of the transdermal drug delivery system.

(15) The method for treatment of an eyelid disease according to the above (9), wherein the eyelid disease is at least one selected from the group consisting of chalazion, blepharitis and meibomian gland dysfunction.

(16) A method for treatment of at least one eyelid disease selected from the group consisting of chalazion, blepharitis and meibomian gland dysfunction comprising topically administering a transdermal drug delivery system to a skin surface of an eyelid of a patient in need thereof, wherein the transdermal drug delivery system comprises an acrylic pressure sensitive adhesive provided on a support, and wherein the acrylic pressure sensitive adhesive comprises clobetasol propionate.

BRIEF DESCRIPTION OF THE DRAWINGS

FIG. 1 shows the experimental apparatus for in vitro permeation experiment, as described in Experimental Example 1.

DETAILED DESCRIPTION OF THE INVENTION

The transdermal drug delivery systems of the present invention, also referred to as "patch" preparations, are topically administratable for treatment of diseases of the eyelid, such as chalazion, blepharitis, meibomian gland dysfunction, allergic conjunctivitis, vernal keratoconjunctivitis and atopic keratoconjunctivitis.

A detailed description of the invention is provided below.

The transdermal drug delivery system of the present invention is a percutaneously absorptive preparation which enables delivery of a therapeutically effective amount of the active agent by application thereof to the skin surface, including the surface of an eyelid. A skin surface including the surface of an eyelid includes a front surface of an upper eyelid, a lower eyelid or both eyelids, or skin surfaces of these eyelids and skin surfaces around them.

Therefore, the transdermal drug delivery system according to the present invention preferably has a form capable of being applied along a skin surface of the upper eyelid, the lower eyelid or both eyelids. Specific examples of such a form include forms such as a rectangle, an ellipse, a crescent, a circle, a horseshoe and a ring along the form of the front surface(s) of the eyelid(s).

The transdermal drug delivery system of the present invention comprises a steroid as an active agent.

The steroid according to the present invention may be any steroid which is pharmaceutically acceptable, in particular, clobetasol, betamethasone, amcinonide, loteprednol, or any pharmaceutically acceptable ester thereof. However, the steroid according to the present invention is not prednisolone or dexamethasone. The pharmaceutically acceptable ester according to the present invention may include, although is not limited to, compounds having a linear or branched chain comprising 1 to 8 carbon atoms, such as at the 17-position and/or 21-position of clobetasol and betamethasone, e.g., lactate, butyrate, isobutyrate, acetate, formate and valerate, or propionate, dipropionate or etabonate. The steroid is preferably clobetasol propionate, clobetasol butyrate, betamethasone dipropionate, loteprednol etabonate or amcinonide, most preferably clobetasol propionate. It is expected that clobetasol butyrate and clobetasol propionate will behave similarly.

Clobetasol, betamethasone, amcinonide, loteprednol, and the pharmaceutically acceptable esters thereof may be prepared by conventional methods, such as those described in U.S. Pat. No. 3,721,687, U.S. Pat. No. 4,158,055, GB 1047519, WO 89/03390 and P. Druzgala, et al., *Soft Drugs-10. Blanching Activity and Receptor Binding Affinity of a New Type of Glucocorticoid: Loteprednol Etabonate*, J. Steroid Biochem., Vol. 38, No. 2, pp. 149-154, 1991, the contents of which are incorporated herein by reference.

While the administration route and the dose may vary depending on a symptom, age and body weight of a subject, the concentration of the active agent in the transdermal drug delivery system of the present invention is about 0.00005 to 20 w/w %, preferably 0.0005 to 10 w/w %, more preferably 0.005 to 5 w/w % of the total weight of the transdermal drug delivery system, and is administered for 2 hours to 2 days, preferably at least 2 hours a day. The amount of steroid in the transdermal drug delivery system is 0.00005 to 35 parts by weight, preferably 0.0005 to 15 parts by weight, more preferably 0.005 to 7 parts by weight per 100 parts by weight of the pressure-sensitive adhesive The transdermal drug delivery system of the present invention may comprise a pressure-sensitive adhesive layer containing the active agent, wherein the pressure-sensitive adhesive layer is provided on a support. See U.S. Patent Publication No. 2010/0150992, the contents of which are incorporated herein by reference.

Examples of the pressure-sensitive adhesive used in the transdermal drug delivery system of the present invention include acrylic pressure-sensitive adhesives, rubber-based pressure-sensitive adhesives and silicone-based pressure-sensitive adhesives. Examples of the rubber-based pressure-sensitive adhesives include those comprising a rubbery elastic substance such as natural rubber, a styrene-isoprene-styrene block copolymer, polyisobutylene, polybutene or polyisoprene as an adhesive base.

The rubber-based pressure-sensitive adhesive is a composition obtained by adding a tackifier such as, for example, a rosin resin, terpene resin, coumarone-indene resin or petroleum resin to the rubbery elastic substance that is the adhesive base. To the adhesive base, as needed, may be added various kinds of additives, for example, a softening agent such as liquid polybutene, liquid polyisobutylene or mineral oil; a filler such as titanium oxide or zinc oxide; an antioxidant (stabilizer) such as butylhydroxytoluene or propyl gallate; and the like. The tackifier is used in a proportion of generally 10 to 400 parts by weight, preferably 50 to 300 parts by weight, more preferably 70 to 200 parts by weight per 100 parts by weight of the rubbery elastic substance.

The transdermal drug delivery system of the present invention may be made by employing a coating method of a solution of the pressure-sensitive adhesive, or a hot-melt method, or a calendering method or the like. In the coating method of the pressure-sensitive adhesive solution, the patch preparation is prepared by a process in which a solution containing the active agent and pressure-sensitive adhesive components in an organic solvent is coated on a releasable liner or support and dried. Examples of the organic solvent include toluene, ethyl acetate and hexane.

In the hot-melt method, the patch preparation is prepared by, for example, the following process. After the pressure-sensitive adhesive components other than the active agent are heated and stirred under purging with nitrogen to melt them, the temperature of the resultant melt is lowered, and the active agent is then added to uniformly mix the respective components. The pressure-sensitive adhesive composition containing the active agent is then spread on a releasable liner by a hot-melt coater, and a support is laminated thereon.

In the calendering method, the patch preparation is prepared by, for example, the following process. After the rubbery elastic substance is kneaded the temperature thereof is lowered, and the tackifier is then added to conduct kneading. After the temperature of the kneaded product is then further lowered, the softening agent is added to conduct kneading, and lastly the active agent is added to conduct kneading, thereby preparing a pressure-sensitive adhesive composition. This pressure-sensitive adhesive composition is spread on a releasable liner, and a support is laminated thereon. Temperature conditions, kneading time and the like may be suitably changed according to the kind of the rubbery elastic substance, the formulation of the pressure-sensitive adhesive composition, and the like. In general, the pressure-sensitive adhesive composition is coated on the releasable liner. However, the composition may be coated on the support, and the releasable liner may be laminated as a coating material as needed.

Among the rubber-based pressure-sensitive adhesives, are preferred those obtained by using a styrene-isoprene-styrene block copolymer (hereinafter may be abbreviated as "SIS" in some cases) as a main adhesive base and, as needed, blending other rubbery elastic substances or the like together with the tackifier from the viewpoints of stability, percutaneous absorptivity and percutaneous permeability of the active agent, tackiness, and the like.

The acrylic pressure-sensitive adhesives include (co)polymers of at least one alkyl (meth)acrylate and copolymers of an alkyl (meth)acrylate and a functional monomer and/or vinyl ester monomer copolymerizable with this ester. The alkyl (meth)acrylate is used in a proportion of generally 50 to 100% by weight, preferably 60 to 97% by weight. The functional monomer is used in a proportion of generally 0 to 30% by weight, preferably 2 to 10% by weight. The vinyl ester monomer is used in a proportion of generally 0 to 40% by weight, preferably 5 to 30% by weight.

The number of carbon atoms of the alkyl group moiety in the alkyl (meth)acrylate is preferably within a range of 4 to 10. Examples of such alkyl (meth)acrylates include butyl acrylate, octyl acrylate, 2-ethylhexyl acrylate, nonyl acrylate and isononyl acrylate. Examples of the functional monomer include (meth)acrylic acids having a functional group. Specific examples thereof include acrylic acid, methacrylic acid and 2-hydroxyethylacrylic acid. Examples of the vinyl ester monomer include vinyl acetate and vinyl laurate.

The acrylic pressure-sensitive adhesive is generally synthesized by solution polymerization, suspension polymerization and emulsion polymerization. A patch preparation may be prepared by dispersing or dissolving the active agent in a solution or emulsion of the acrylic pressure-sensitive adhesive, applying the resultant solution or dispersion on to a releasable liner or support and drying it. This acrylic pressure-sensitive adhesive is preferably crosslinked by adding a small amount of a crosslinking agent.

Examples of the silicone-based pressure-sensitive adhesives include those comprising bifunctional or trifunctional polysiloxane, or the like as a main component. A patch preparation may be prepared by dispersing or dissolving the active agent in the silicone-based pressure-sensitive adhesive or a solution thereof, applying or spreading the resultant solution or dispersion on to a releasable liner or support.

The support preferably has flexibility to an extent that it can be brought into close contact with a skin surface including a front surface of a rolling eyelid. The support is preferably such that it does not absorb the active agent, and the active agent is not released from the side of the support. As specific examples of the support, may be mentioned nonwoven fabrics, fabrics, films (including sheets), porous bodies, foamed bodies, paper, and composite materials obtained by laminating a film on a nonwoven fabric or fabric. However, the support is not limited thereto.

Examples of a material for the nonwoven fabric used as the support include polyolefin resins such as polyethylene and polypropylene; polyester resins such as polyethylene terephthalate, polybutylene terephthalate and polyethylene naphthalate; and besides rayon, polyamide, poly(ester ether), polyurethane, polyacrylic resins, polyvinyl alcohol, styrene-isoprene-styrene copolymers, and styrene-ethylene-propylene-styrene copolymers. As examples of a material for the fabric, may be mentioned cotton, rayon, polyacrylic resins, polyester resins and polyvinyl alcohol. However, the materials are not limited thereto.

Examples of a material for the film used as the support include polyolefin resins such as polyethylene and polypropylene; polyacrylic resins such as polymethyl methacrylate and polyethyl methacrylate; polyester resins such as polyethylene terephthalate, polybutylene terephthalate and polyethylene naphthalate; and besides cellophane, polyvinyl alcohol, ethylene-vinyl alcohol copolymers, polyvinyl chloride, polystyrene, polyurethane, polyacrylonitrile, fluororesins, styrene-isoprene-styrene copolymers, styrene-butadiene rubber, polybutadiene, ethylene-vinyl acetate copolymers, polyamide, and polysulfone. However, the materials are not limited thereto.

Examples of paper include impregnated paper, coated paper, wood free paper, kraft paper, Japanese paper, glassine paper and synthetic paper. As examples of the composite materials, may be mentioned composite materials obtained by laminating the above-described film on the above-described nonwoven fabric or fabric.

The active agent is used in a proportion of generally 0.00005 to 35 parts by weight, preferably 0.0005 to 15 parts by weight, more preferably 0.05 to 7 parts by weight per 100 parts by weight of the pressure-sensitive adhesive. If the proportion of the active agent is too low, it is difficult to achieve sustainedly sufficient drug efficacy. If the proportion is too high, crystals may be deposited to lower adhesion in some cases.

The transdermal drug delivery system for treatment of ophthalmic diseases according to the present invention may be prepared in accordance with conventional methods known in the art, such as the processes described above, and those described in U.S. Patent Publication No. 2010/0150992, the contents of which have previously been incorporated by reference.

Unless the intended purpose of use is affected adversely, the transdermal drug delivery systems of the present invention may contain or may be used together with other appropriate pharmacologically effective substances.

A specific embodiment of the present invention is a transdermal drug delivery system comprising 0.00005 to 20 w/w %, preferably 0.0005 to 10 w/w %, more preferably 0.005 to 5 w/w % of a steroid and a 99.99995 to 80 w/w %, 99.995 to 90 w/w %, more preferably 99.995 to 95 w/w % of a pressure-sensitive adhesive.

Such compositions preferably comprise about 0.5 w/w % clobetasol propionate and about 99.5 w/w % acrylic pressure-sensitive adhesive, and are to be administered for 8 hours a day to each affected eye.

The transdermal drug delivery system according to the present invention may comprise a pharmacologically acceptable carrier, excipient or diluent which is known per se for transdermal drug delivery systems, including but not limited to a tackifier, plasticizer, antioxidant, filler, crosslinking agent, solubilizing agent, percutaneous absorption enhancer, preservative, and ultraviolet absorber.

The transdermal drug delivery system of the present invention may be administered to a mammal which is or may be suffering from a disease of the eyelid (e.g., a human, rabbit, dog, cat, cattle, horse, monkey).

The present invention is further illustrated in detail by the following Formulation Examples and Experimental Examples. These Formulation Examples and Experimental Examples are merely illustrative, and are not intended to limit the scope of the present invention.

FORMULATION EXAMPLE 1

An SIS (styrene-isoprene-styrene)-based pressure sensitive adhesive was obtained by blending 100 parts by weight of a hydrogenated rosin ester resin (trade name "Pinecrystal KE311") as a tackifier with 100 parts by weight of a styrene-isoprene-styrene block copolymer (trade name "Quintac 3520"). 99.0 w/w % of the SIS-based pressure sensitive adhesive (Pinecrystal KE311/Quintac 3520 ratio is 50%/50% (w/w)) and 1.0 w/w % of clobetasol propionate were dissolved in toluene to obtain a coating fluid having a solid content of 50% by weight. This coating fluid was coated on release paper so as to give a dry coat thickness of 40 µm. After drying, a support (polyester film having a thickness of 12 µm) was laminated to provide a patch preparation.

FORMULATION EXAMPLE 2

0.005 g of a crosslinking agent (chelate-type crosslinking agent; trade name "NISSETSU CK-401"), and 0.05 g of clobetasol were added to 12.363 g (Solids: 4.945 g) of an acrylic pressure sensitive adhesive [trade name "NISSETSU PE-300"; alkyl (meth)acrylate-vinyl acetate copolymer; pressure sensitive adhesive solution having a solid content of 40% by weight (ethyl acetate/toluene mixed solvent)] to prepare a coating fluid having a concentration of 57.3% by weight. This coating fluid was coated on release paper so as to give a dry coat thickness of 80 µm. After drying, a support (polyester film having a thickness of 12 µm) was laminated to provide a patch preparation.

FORMULATION EXAMPLE 3

A pressure-sensitive adhesive solution (coating fluid) having a solid content of 40% by weight was obtained by dissolving 40.5 g of a styrene-isoprene-styrene block copolymer (trade name "SIS5000") as a rubbery elastic substance, 40.5 g of a terpene resin (trade name "YS Resin 115ON") as a tackifier and 10 g of clobetasol propionate in 150 g of toluene. This coating fluid was coated on release paper so as to give a dry coat thickness of 40 µm. After drying, a support (polyester film having a thickness of 12 µm) was laminated to provide a patch preparation.

FORMULATION EXAMPLE 4

Four hundred grams of a styrene-isoprene-styrene block copolymer (trade name "Cariflex TR-1107") as a rubbery elastic substance, 400 g of a terpene resin (YS Resin 1150N) as a tackifier, 125 g of liquid paraffin as a softening agent and 5 g of clobetasol propionate were uniformly mixed by kneading using a heating kneader. After the kneading, the mixture was spread on a silicone surface of a releasable liner, on one surface of which had been subjected to a silicone treatment, by means of a calender, so as to give a thickness of 200 µm. A support (polyester film having a thickness of 12 µm) was then laminated thereon to provide a patch preparation.

EXPERIMENTAL EXAMPLE 1

In vitro permeation study through hairless mouse skin to investigate the skin permeability of clobetasol propionate, amcinonide, betamethasone dipropionate, loteprednol etabonate, dexamethasone, prednisolone acetate and its metabolite (prednisolone).

Materials and Methods

Steroid patches were prepared according to the following procedure. The steroid (clobetasol propionate, amcinonide, betamethasone dipropionate, loteprednol etabonate, dexamethasone, or prednisolone acetate) was weighed in a clear polypropylene cup. 2 mL of ethyl acetate was added, and dispersed by ultrasonic wave using an ultrasonicator. DURO-TAK® 87-4098 was carefully added in the clear polypropylene cup. The components were mixed using a spatula, and then the lid of the cup was closed to avoid evaporation. A coating bar was adjusted to about 370 µm to control the thickness. The product material was carefully dispensed onto release liner near the coating bar. The coating process was started by moving the coating bar with the hand. The coated sheet was transferred to the oven and heated at 80° C. for 10±1 minutes. The dried sheet was removed from the oven, and laminated with the polyethylene terephthalate film. The thickness of the patch was checked.

Table 1 shows the components of the steroid (clobetasol propionate, dexamethasone, or prednisolone acetate) patches.

TABLE 1

Components of steroid patches

| Components | Function | Amount (%, w/w) | Solid weight (g) |
|---|---|---|---|
| Steroid: clobetasol propionate, amcinonide, betamethasone dipropionate, loteprednol etabonate, dexamethasone, or prednisolone acetate | Active | 5.0 | 0.15 |
| DURO-TAK ® 87-4098 *[1] | Adhesive | 95.0 | 2.85 |
| Total weight = | | 100 | 3.0 |

*[1] Duro-Tak 87-4098 is acrylate-vinylacetate pressure sensitive adhesive

The abdominal skin of 6 hairless, 8 week old, female mice were used for in vitro skin permeation experiment. The skin was mounted on an in vitro skin permeation experimental apparatus, as shown in FIG. 1. (Horizontal cell, effective volume: 5 mL, effective area: 0.64 cm$^2$). The clobetasol propionate 5% patch, amcinonide 5% patch, betamethasone dipropionate 5% patch, loteprednol etabonate 5% patch, dexamethasone 5% patch, or prednisolone acetate 5% patch was applied to the stratum corneum surface and 5 mL of 40% polyethylene glycol 400 solution was added to the receptor cell to maintain the sink condition. The experimental temperature was controlled at 37° C., and 400 µL it of receptor solution was sampled at 1, 2, 3, 4, 5, 6, 9, 12, 22, 28, 34 and 48 hours. Thereafter, the same amount of the 40% polyethylene glycol 400 solution was added to the receptor cell. The concentration of each steroid in the sampled receptor solution was analyzed with HPLC.

Results and Discussion

Table 2 summarizes the steady-state penetration rate and lag-time of the steroids across the hairless mouse skin.

TABLE 2

The steady-state penetration rate and lag-time of six steroids across the hairless mouse skin.

| | | dQ/dt [µg/cm$^2$/h] | $t_d$ [h] |
|---|---|---|---|
| Amcinonide 5% patch | Amcinonide | 0.159 | 3.5 |
| Clobetasol propionate 5% patch | Clobetasol propionate | 0.108 | 2.7 |
| Loteprednol etabonate 5% patch | Loteprednol etabonate | 0.095 | 3.7 |
| Betamethasone dipropionate 5% patch | Betamethasone dipropionate | 0.048 | 4.7 |
| Dexamethasone 5% patch | Dexamethasone | 0.014 | 15.1 |
| Prednisolone acetate 5% patch | Prednisolone acetate | 0.007 | 17.7 |
| | Prednisolone | 0.008 | 18.4 |

*Mean (n = 2),
dQ/dt: Steady-state penetration rate,
$t_d$: Lag time

The steady-state penetration rate of amcinonide, clobetasol, loteprednol and betamethasone were 20 and 10, 14 and 8, 12 and 7, 6 and 3 times higher than that of prednisolone and dexamethasone, respectively, which are used as ophthalmic ointments. The lag-time of amcinonide, clobetasol, loteprednol, and betamethasone were 5 and 4, 7 and 6, 5 and 4, 4 and 3 times shorter than prednisolone and dexamethasone, respectively. It is expected that clobetasol butyrate would behave similarly to clobetasol propionate. The reason for the difference in the skin permeation among the six steroids may depend on the chemical characteristics, such as the chemical structure of the steroid compounds.

Prior to the present invention, it has been unknown whether different steroids have differing permeation rates in a transdermal patch when applied to the eye. The present inventors have discovered that amcinonide, clobetasol, loteprednol and betamethasone surprisingly penetrate well into the skin, when compared to ophthalmic steroids such as prednisolone acetate and dexamethasone.

EXPERIMENTAL EXAMPLE 2

In vivo pharmacology study to compare the efficacy of steroid patches on eyelid inflammation induced by carrageenan with a commercially available ophthalmic ointment comprising prednisolone acetate.

Materials and Methods

A clobetasol propionate 5% patch, amcinonide 5% patch, loteprednol etabonate 5% patch, and betamethasone dipropionate 5% patch were made in accordance with the description of Experimental Example 1 and Table 1.

The commercially available ophthalmic ointment is a Prednisolone 0.25% ointment.

Additionally, a placebo patch was employed as the control, which includes the same ingredients without the active agent (steroid).

The subjects of the experiment were male rats (n=47), aged about 8 weeks, weighing about 180 g.

Administration of Test Articles

The animals in the patch and ointment groups were anesthetized by inhalation of Isoflurane. Under anesthesia, the fur at the skin around the right lower eyelid was clipped with an electric hair clipper and an electric shaver until the skin was smooth. On the next day, a steroid patch with an area of 0.4 cm$^2$ (0.8 cm long×0.5 cm wide, 172.8 µg/0.4 cm$^2$) was applied to right lower eyelid, followed by application of a cover tape on the patch to prevent detachment from the skin. The patch was removed 8 hours after the application.

Preparation of Carrageenan Solution, and Induction of Conjunctival Edema by Carrageenan and Excision of Conjunctival Edema Carrageenan was dissolved in physiological saline in 40° C. hot bath to make the concentration at 1%, and the solution was kept in 40° C. hot bath during the injection of carrageenan. The carrageenan solution was prepared before use every operation day.

The animals were anesthetized by the inhalation of Isoflurane. After the patch removal, 50 µL of 1% carrageenan was injected to the right lower eyelid. Four hours later, the rat was sacrificed by the inhalation of carbonic anhydride and a portion of edema was excised by scissors and weighed by an electric scale.

For the reference drug, 20 µg of ointment (50 µg prednisolone) was applied to the right eyelid at 8 and 4 hours before carrageenan injection, as shown below.

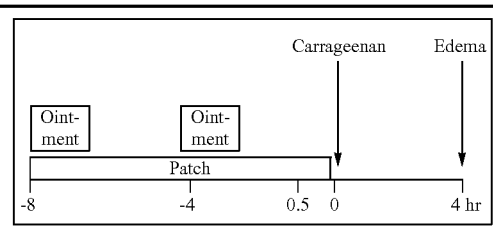

Results and Discussion

The weight of eyelid edema in the placebo patch group was 67.0±3.9 (mg, mean±S.E. n=8). The weight of eyelid edema in the clobetasol, amcinonide, loteprednol and betamethasone 5% patch groups were 34.0±3.0 (n=9), 44.4±1.6 (n=8), the back followed by application of a cover tape on the patch so that it did not detach. The patch was removed at 8 hrs after the application. The application sites were observed at 1 hr and 16 hrs after removal of the patch on Day 1 and continuing the same procedure periodically up to 3 days, as shown below.

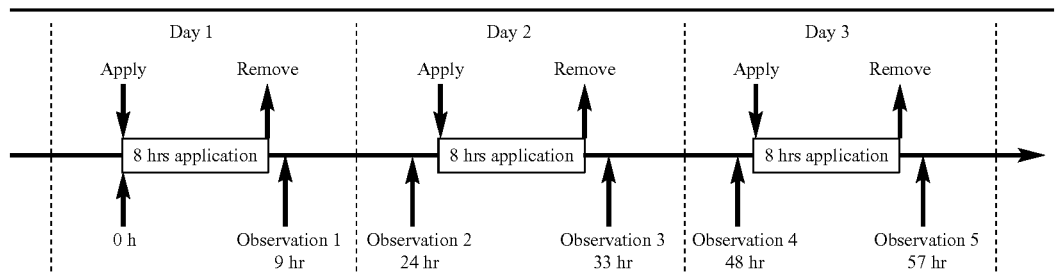

40.9±4.8 (n=8) and 41.6±2.4 (n=8), respectively, and they significantly inhibited edema formation by 49.3% (p<0.0001), 33.7% (p<0.05), 39.0% (p<0.01) and 37.9% (p<0.01), respectively. It is expected that clobetasol butyrate would behave similarly to clobetasol propionate. The weight of eyelid edema in the prednisolone ointment group was 62.8±5.4 (n=6) and prednisolone did not significantly inhibit edema (p<0.38) (Table 3).

Thus, is it suggested that the steroid patches are more therapeutically effective on treatment of eyelid diseases, compared to ophthalmic ointments.

TABLE 3

Effect of steroid patches and prednisolone ointment on carrageenan-induced eyelid edema

| Groups | Edema weight [mg] | Inhibition [%] |
|---|---|---|
| Placebo patch | 67.0 ± 3.9 | — |
| Amcinonide 5% patch | 44.4 ± 1.6 | 33.7 |
| Clobetasol propionate 5% patch | 34.0 ± 3.0 | 49.3 |
| Loteprednol etabonate 5% patch | 40.9 ± 4.8 | 39.0 |
| Betamethasone dipropionate 5% patch | 41.6 ± 2.4 | 37.9 |
| Prednisolone 0.25% ophthalmic ointment | 62.8 ± 5.4 | 6.3 |

Mean ± S.E. (n = 6-9)
* p < 0.05,
** p < 0.01,
*** p < 0.001

EXPERIMENTAL EXAMPLE 3

Evaluation of the primary skin irritation of steroid patches when administered topically in male New Zealand White rabbits.

Materials and Methods

A clobetasol propionate 5% patch, amcinonide 5% patch, loteprednol etabonate 5% patch and betamethasone dipropionate 5% patch were made in accordance with the description of Experimental Example 1 and Table 1.

One day before the patch application, the New Zealand White rabbits (n=4) were anesthetized by the inhalation of isoflurane using the vaporizer. Under anesthesia, the fur around the back was clipped with an electric hair clipper and an electric shaver until the skin was exposed. Just prior to test patch application, each rabbit received a "#" pattern epidermal abrasions with sterile needle at one test site while the skin at opposite site remained intact. Day 1: Each steroid patch with an area of 4 cm² (2 cm long×2 cm wide) was applied to The skin reaction at each patch application site was evaluated for the severity of erythema and edema (Table 4).

TABLE 4

Grading of Skin Reactions, based on Test Guideline 404.
OECD Guidelines for Testing of Chemicals (2002)

| | Grade |
|---|---|
| Erythema and Eschar Formation | |
| No erythema | 0 |
| Very slight erythema (barely perceptible) | 1 |
| Well defined erythema | 2 |
| Moderate to severe erythema | 3 |
| Severe erythema (beef redness) to eschar formation preventing grading of erythema | 4 |
| Edema Formation | |
| No edema | 0 |
| Very slight edema (barely perceptible) | 1 |
| Slight edema (edges of area well defined by definite raising) | 2 |
| Moderate edema (raised approximately 1 mm) | 3 |
| Severe edema (raised more than 1 mm and extending beyond area of exposure) | 4 |

The cumulative irritancy index was calculated for the test patches by dividing the sum of the total irritation score by the number of observations. Categories of primary dermal irritation index for the test patches were categorized based on the index in Table 5.

TABLE 5

Irritation Response Categories in Rabbit, based on Test for Primary Skin Irritants Recommended by the Food and Drug Administration, Federal Register USA 37 [244]: 27035, 1972.

| Response Category | C.I.I. |
|---|---|
| Negligible | 0 to 0.4 |
| Slight | 0.5 to 1.9 |
| Moderate | 2 to 4.9 |
| Severe | 5 to 8 |

Results and Discussion

The C.I.I. of surgical tape as a positive control was evaluated. The C.I.I. of lotepredonl patch was calculated to be "0" and "No irritation" was evaluated. The C.I.I of amcinonide, betamethasone, clobetasol and placebo patches were calculated to be "0.1 to 0.3" and "Negligible Irritation" was evaluated. There were not differences in irritation score of 4 steroid patches compared to the placebo patch. There was no difference in skin irritation between intact skin and abraded skin (Table 6).

TABLE 6

C.I.I. of steroid patches by 3-day application on rabbit skin

| Treatments | C.I.I. | Response Category |
|---|---|---|
| Amcinonide 5% patch | 0.2 | Negligible Irritation |
| Betamethasone dipropionate 5% patch | 0.1 | Negligible Irritation |
| Clobetasol propionate 5% patch | 0.1 | Negligible Irritation |
| Loteprednol etabonate 5% patch | 0.0 | Non Irritation |
| Placebo patch | 0.3 | Negligible Irritation |
| Surgical tape (3M Transpore ™) | 1.6 | Slight Irritation |

The C.I.I. of the four steroid patches as calculated to be less than 0.3 indicating negligible rabbit skin irritation. It is expected that clobetasol butyrate would behave similarly to clobetasol propionate.

EXPERIMENTAL EXAMPLE 4

Study of dose-response effect of clobetasol propionate patch on rat eyelid inflammation induced by carrageenan.
Materials and Methods Clobetasol propionate patches were made in accordance with the description of Experimental Example 1, and Tables 7-9 below.

TABLE 7

Components of Clobetasol propionate 0.5% patch

| Components | Function | Amount (%, w/w) | Solid weight (g) |
|---|---|---|---|
| Clobetasol propionate | Active | 0.5 | 0.025 |
| DURO-TAK ® 87-4098 *[1] | Adhesive | 99.5 | 4.975 |
| Total weight = | | 100 | 5.0 |

*[1] Duro-Tak 87-4098 is acrylate-vinylacetate pressure sensitive adhesive

TABLE 8

Components of Clobetasol propionate 0.05% patch

| Components | Function | Amount (%, w/w) | Solid weight (g) |
|---|---|---|---|
| Clobetasol propionate | Active | 0.05 | 0.0025 |
| DURO-TAK ® 87-4098 *[1] | Adhesive | 99.95 | 4.9975 |
| Total weight = | | 100 | 5.0 |

*[1] Duro-Tak 87-4098 is acrylate-vinylacetate pressure sensitive adhesive contained in ethyl acetate.

TABLE 9

Components of Clobetasol propionate 0.005% patch

| Components | Function | Amount (%, w/w) | Solid weight (g) |
|---|---|---|---|
| Clobetasol propionate | Active | 0.005 | 0.00025 |
| DURO-TAK ® 87-4098 *[1] | Adhesive | 99.995 | 4.99975 |
| Total weight = | | 100 | 5.0 |

*[1] Duro-Tak 87-4098 is acrylate-vinylacetate pressure sensitive adhesive contained in ethyl acetate.

The animals (8 week old male rats) in the patch and ointment groups were anesthetized by inhalation of Isoflurane. Under anesthesia, the fur at the skin around the right lower eyelid was clipped with an electric hair clipper and an electric shaver until the skin was smooth. On the next day, clobetasol 0.005%, 0.05% or 0.5% patch with an area of 0.4 cm$^2$ (0.8 cm long×0.5 cm wide, 17.28, 1.728, 0.1728 μg/0.4 cm$^2$) was applied to the right lower eyelid followed by application of a cover tape on the patch to prevent detachment from the skin. The patch was removed at 8 hrs after the application.

Carrageenan was dissolved in physiological saline in 40° C. hot bath to make the concentration at 1%, and the solution was kept in 40° C. hot bath during the injection of carrageenan. The carrageenan solution was prepared before use every operation day.

The animals were anesthetized by the inhalation of Isoflurane. After the patch removal, 50 μL of 1% carrageenan was injected to the right lower eyelid. Four hours later, the rat was sacrificed by the inhalation of carbonic anhydride and a portion of edema was excised by scissors and weighed by an electric scale.

For the reference drug, 5 mg of ointment (2.5 μg/5 mg, 0.5 mg clobetasol in 1 g ointment) was applied to the right eyelid at 8 and 4 hrs before carrageenan injection, as shown below.

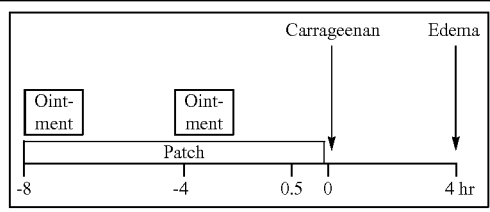

Results and Discussion

The weight of eyelid edema in the placebo patch group was 59.7±4.0 mg (mean±S.E., n=8). The weight of eyelid edema in clobetasol 0.005%, 0.05% and 0.5% patch groups was 35.1±2.3 (n=8), 31.8±3.2 (n=8) and 24.8±2.5 mg (n=8), respectively. Clobetasol at all concentrations significantly inhibited edema compared to the placebo (p<0.001) and their inhibitions were 41.2%, 46.7% and 58.5%, respectively. Please see Table 10. It is expected that clobetasol butyrate would behave similarly to clobetasol propionate.

The weight of eyelid edema in the clobetasol 0.05% ointment group was 35.7±2.8 (n=7) and 0.05% ointment significantly inhibited it by 40.2% (p<0.001). The clobetasol 0.5% patch was significantly superior to 0.05% ointment (p<0.05%).

It is suggested that a clobetasol patch has the same or more potency than 0.05% ointment on eyelid diseases.

TABLE 10

Effect of clobetasol patch and clobetasol ointment on carrageenan-induced eyelid edema

| Groups | Edema weight [mg] | Inhibition [%] |
|---|---|---|
| Placebo patch | 59.7 ± 4.0 | — |
| Clobetasol propionate 0.005% patch | 35.1 ± 2.3 | 41.2 |
| Clobetasol propionate 0.05% patch | 31.8 ± 3.2 | 46.7 |
| Clobetasol propionate 0.5% patch | 24.8 ± 2.5 | 58.5 |
| Clobetasol propionate 0.05% ointment | 35.7 ± 2.8 | 40.2 |

Mean ± S.E. (n = 7-8)
* p < 0.001 vs Placebo,
# p < 0.05% vs Ointment 0.05

EXPERIMENTAL EXAMPLE 5

Study of dose-response toxicity of clobetasol propionate patch by 14 day-repeated application to rats.
Materials and Methods Clobetasol propionate 0.5%, 0.05% and 0.005% patches were made in accordance with Experimental Example 4 and Tables 7-9.

A placebo patch was made in accordance with Table 11 below.

TABLE 11

Components of placebo Patch

| Components | Function | Amount (%, w/w) | Solid weight (g) |
|---|---|---|---|
| DURO-TAK ® 87-4098 *[1] | Adhesive | 100 | 5.0 |
| Total weight = | | 100 | 5.0 |

*[1] Duro-Tak 87-4098 is acrylate-vinylacetate pressure sensitive adhesive contained in ethyl acetate.

The rats (9 week old male rats) were anesthetized by the inhalation of isoflurane. Under anesthesia, the fur at the skin around the back was clipped with an electric hair clipper and an electric shaver until the skin is exposed. The clobetasol propionate patch at 0.5%, 0.05% or 0.005% was applied to a defined area (20 cm$^2$, 4×5 cm, 860, 86 or 8.6 μg clobetasol propionate/patch, respectively) on the skin of the back daily for 14 days. The patch was protected by a bandage tape on the patch. The patch was removed at 8 hrs after the application. Clobetasol propionate 0.05% ointment was applied to a defined area (20 cm$^2$, 4×5 cm, 127 μg clobetasol propionate/ 253 mg ointment) on the skin of the back at a dose of 47 mg/100 g body weight daily for 14 days.

1) Toxicological Signs of Skin (Daily)

Observation of toxicological signs of skin was carried out daily before and after the application.

Items
hair growth, skin atrophy of epidermis and dermis, erythema, and edema
  Grade of score
  0; none, 1; very slight, 2; slight, 3; moderate, 4; severe
2) Body Weight (Daily)
Body weight measurement was carried out daily before the application.

3) Skin Fold Thickness (Days 1, 3, 7, 10 and 14)

For measurement of the skin fold thickness, an electric caliper with 10 mm wide was set on the skin in the center of application site and skin thickness was measured by sliding measurement body.

4) Histological Examination of Skin (Day 14)

After 8 hr application at Day 14, the animals were sacrificed by suction of $CO_2$. The skin at application site and non-application site nearby were excised and the skin thickness was measured by the electric caliper.

Results and Discussions
Toxicological Signs of Skin

Table 12 shows the difference in total toxicological score of skin between Days 1 and 14. Clobetasol 0.05% ointment induced skin atrophy and hair growth inhibition and total toxicological score increased from Day 8 and its score increased by 2.0 at Day 14. All patch (0.005%, 0.05% and 0.5%) groups had no irritation, no atrophy, and normal hair growth.

TABLE 12

The difference in total toxicological score of skin between Days 1 and 14.

| | Placebo Patch | 0.005% CP Patch | 0.05% CP Patch | 0.5% CP Patch | 0.05% CP ointment [Taro] |
|---|---|---|---|---|---|
| Day 1 | 0 ± 0 | 0 ± 0 | 0 ± 0 | 0 ± 0 | 0 ± 0 |
| Day 14 | 0.3 ± 0.4 | 0 ± 0 | 0 ± 0 | 0 ± 0 | 2.0 ± 0.0 |

Mean ± S.D. (n = 4)

Body Weight

Table 13 shows the difference in body weight between Days 1 and 14. The body weights in 0.005%, 0.05% and 0.5% patch groups increased by 8.5, 12.0 and 4.7 g at Day 14, respectively. On the other hand, the body weight in 0.05% ointment group decreased by 40.1 g at Day 14.

TABLE 13

The difference in body weight between Days 1 and 14.

| | Placebo Patch | 0.005% CP Patch | 0.05% CP Patch | 0.5% CP Patch | 0.05% CP ointment [Taro] |
|---|---|---|---|---|---|
| Day 1 | 287.5 ± 9.0 g | 283.1 ± 10.3 g | 291.2 ± 9.1 g | 297.0 ± 7.1 g | 294.8 ± 7.3 g |
| Day 14 | 295.9 ± 13.2 g | 291.6 ± 12.0 g | 303.2 ± 13.1 g | 301.7 ± 5.3 g | 254.9 ± 9.1 g |
| Day 14 – Day 1 | +8.4 g | +8.5 g | +12.0 g | +4.7 g | −40.1 g |

Mean ± S.D. (n = 4)

Skin Fold Thickness

Table 14 shows the difference in skin thickness between Days 1 and 14. The skin thicknesses in 0.005%, 0.05% and 0.5% patch groups dose-dependently decreased by 0.13, 0.22 and 0.66 mm at Day 14, respectively. The skin thickness in 0.05% ointment group also decreased by 1.05 mm at Day 14.

TABLE 14

The difference in skin thickness between Days 1 and 14

|  | Placebo Patch | 0.005% CP Patch | 0.05% CP Patch | 0.5% CP Patch | 0.05% CP ointment [Taro] |
|---|---|---|---|---|---|
| Day 1 | 2.73 ± 0.13 mm | 2.83 ± 0.21 mm | 2.80 ± 0.21 mm | 2.87 ± 0.16 mm | 2.85 ± 0.10 mm |
| Day 14 | 2.83 ± 0.40 mm | 2.70 ± 0.33 mm | 2.58 ± 0.15 mm | 2.27 ± 0.20 mm | 1.80 ± 0.10 mm |
| Day 14 − Day 1 | +0.10 mm | −0.13 mm | −0.22 mm | −0.60 mm | −1.05 mm |

Mean ± S.D. (n = 4).

INDUSTRIAL APPLICABILITY

Prior to the present invention, it was unknown whether the permeation rate of transdermal drug delivery systems containing a steroid as an active agent differed based upon the active ingredient. Based upon the in vitro permeation study performed by the present inventors, the steroids clobetasol propionate, betamethasone dipropionate, amcinonide and loteprednol etabonate demonstrate surprisingly superior penetration compared to known ophthalmic steroids prednisolone acetate and dexamethasone. Furthermore, in view of the rat pharmacology study performed by the inventors, it was discovered that a transdermal drug delivery system containing one of the above-mentioned steroids as the active agent significantly inhibited eyelid inflammatory edema, while an ophthalmic ointment of prednisolone acetate did not. Accordingly, the present inventors discovered that the above-mentioned steroids, in particular, clobetasol propionate, highly penetrated into tissues from the eyelid application site, and thus, showed more superior efficacy than the ophthalmic ointment of prednisolone acetate, which had poorer penetration.

The invention claimed is:

1. A transdermal drug delivery system for treatment of an eyelid disease comprising a pressure sensitive adhesive layer provided on a support,
    wherein the pressure sensitive adhesive layer comprises a steroid and a pressure sensitive adhesive,
        wherein the steroid is selected from the group consisting of clobetasol propionate, clobetasol butyrate, betamethasone dipropionate, amcinonide, and loteprednol etabonate,
        wherein the pressure-sensitive adhesive is selected from the group consisting of acrylic pressure sensitive adhesives, rubber-based pressure sensitive adhesives and silicone-based pressure sensitive adhesives,
            wherein, if the pressure-sensitive adhesive is an acrylic pressure sensitive adhesive, the acrylic pressure sensitive adhesive is either
                an alkyl (meth)acrylate-vinyl acetate copolymer or
                an acrylate-vinylacetate copolymer,
            wherein, if the pressure-sensitive adhesive is a rubber-based pressure sensitive adhesive, the rubber-based pressure sensitive adhesive is a styrene-isoprene-styrene block copolymer,
    wherein the transdermal drug delivery system has a shape capable of being applied along a skin surface of the upper eyelid, a skin surface of the lower eyelid, or a skin surface of both eyelids, and
    wherein the transdermal drug delivery system is capable of administering a therapeutically effective amount of the steroid to the eyelid with negligible irritation.

2. The transdermal drug delivery system according to claim 1, wherein the pressure-sensitive adhesive is an acrylate-vinylacetate copolymer.

3. The transdermal drug delivery system according to claim 1, wherein the steroid is selected from the group consisting of clobetasol propionate and clobetasol butyrate.

4. The transdermal drug delivery system according to claim 1, wherein the concentration of the steroid is 0.005 to 5 w/w % of the total weight of the transdermal drug delivery system.

5. The transdermal drug delivery system according to claim 1, wherein the eyelid disease is at least one selected from the group consisting of chalazion, blepharitis and meibomian gland dysfunction.

6. A method for treatment of an eyelid disease, comprising topically applying a transdermal drug delivery system to a skin surface of an eyelid of a patient in need thereof in order to administer a therapeutically effective amount of a steroid to the eyelid of the patient with negligible irritation,
    wherein the transdermal drug delivery system comprises a pressure sensitive adhesive layer provided on a support,
    wherein the pressure sensitive adhesive layer comprises the steroid and a pressure sensitive adhesive,
    wherein the steroid is selected from the group consisting of clobetasol propionate, clobetasol butyrate, betamethasone dipropionate, amcinonide, and loteprednol etabonate,
    wherein the pressure-sensitive adhesive is selected from the group consisting of acrylic pressure sensitive adhesives, rubber-based pressure sensitive adhesives and silicone-based pressure sensitive adhesives,
        wherein, if the pressure-sensitive adhesive is an acrylic pressure sensitive adhesive, the acrylic pressure sensitive adhesive is either
            an alkyl (meth)acrylate-vinyl acetate copolymer or
            an acrylate-vinylacetate copolymer, and
        wherein, if the pressure-sensitive adhesive is a rubber-based pressure sensitive adhesive, the rubber-based pressure sensitive adhesive is a styrene-isoprene-styrene block copolymer.

7. The method for treatment of eyelid disease according to claim 6, wherein the pressure-sensitive adhesive is an acrylate-vinylacetate copolymer.

8. The method for treatment of an eyelid disease according to claim 6, wherein the steroid is selected from the group consisting of clobetasol propionate and clobetasol butyrate.

9. The method for treatment of an eyelid disease according to claim 6, wherein the concentration of the steroid is 0.005 to 5 w/w % of the total weight of the transdermal drug delivery system.

10. The method for treatment of an eyelid disease according to claim 6, wherein the eyelid disease is at least one selected from the group consisting of chalazion, blepharitis and meibomian gland dysfunction.

11. The transdermal drug delivery system according to claim 1, wherein the shape capable of being applied along a skin surface of the upper eyelid, a skin surface of the lower eyelid, or a skin surface of both eyelids is a rectangle, an ellipse, a crescent, a circle, a horseshoe or a ring.

12. The method according to claim 6, wherein the transdermal drug delivery system has a shape capable of being applied along a skin surface of the upper eyelid, a skin surface of the lower eyelid, or a skin surface of both eyelids, wherein the shape is a rectangle, an ellipse, a crescent, a circle, a horseshoe or a ring.

13. The transdermal drug delivery system according to claim 1, wherein the steroid is clobetasol propionate.

14. The method for treatment of an eyelid disease according to claim 6, wherein the steroid is clobetasol propionate.

* * * * *